United States Patent [19]

Cummins et al.

[11] 4,335,257

[45] Jun. 15, 1982

[54] PREPARATION OF THE CALCIUM SALT OF ALPHA-HYDROXY-GAMMA-METHYLMER-CAPTOBUTYRIC ACID

[75] Inventors: Earl W. Cummins; Steven I. Gleich; Robert M. Vigilant, all of Wilmington, Del.

[73] Assignee: E. I. Du Pont De Nemours and Company, Wilmington, Del.

[21] Appl. No.: 184,210

[22] Filed: Sep. 5, 1980

[51] Int. Cl.$^3$ ............................................ C07C 149/20
[52] U.S. Cl. ..................................................... 562/581
[58] Field of Search ........................................ 562/581

[56] References Cited

U.S. PATENT DOCUMENTS

| | | | |
|---|---|---|---|
| 2,745,745 | 5/1956 | Blake et al. | 562/581 |
| 2,946,818 | 7/1960 | Anagnostopoulos | 562/581 |
| 3,175,000 | 3/1965 | Gielkens et al. | 562/581 |
| 4,060,535 | 11/1977 | Cinco | 562/581 |

FOREIGN PATENT DOCUMENTS

| | | | |
|---|---|---|---|
| 694610 | 9/1964 | Canada | 562/581 |
| 915193 | 1/1963 | United Kingdom | 562/581 |

*Primary Examiner*—Paul J. Killos

[57] ABSTRACT

This invention relates to a novel process for preparing the calcium salt of α-hydroxy-γ-methylmercaptobutyric acid (MHBA) by contacting solid calcium oxide or calcium hydroxide with liquid MHBA.

14 Claims, No Drawings

PREPARATION OF THE CALCIUM SALT OF ALPHA-HYDROXY-GAMMA-METHYLMERCAPTOBUTYRIC ACID

BACKGROUND OF THE INVENTION

The hydroxy analogue of methionine is a well-known chemical compound which is otherwise described as α-hydroxgy-γ-methylmercaptobutyric acid (MHBA). This compound has nutrient values equivalent to the corresponding amino acid, methionine. The calcium salt of MHBA is also well known, and it is usually in this form that it is used to fortify animal feeds.

In commonly used processes for preparing the calcium salt of MHBA, it has been necessary to isolate the product calcium salt from dilute aqueous solutions. This is done by evaporation of the water to give a slurry of the product calcium salt which is then isolated by filtration and drying. (U.S. Pat. Nos. 2,745,745 and 3,175,000). In applicants' experience, it has often been necessary to evaporate ten to sixteen pounds of water for each pound of product produced. This evaporation step is costly and is becoming even more so as energy costs rise. There is therefore a clear need for a new, economical, and energy-efficient process for preparing this useful feed supplement.

SUMMARY OF THE INVENTION

It has now been found that the calcium salt of α-hydroxy-γ-methylmercaptobutyric acid,

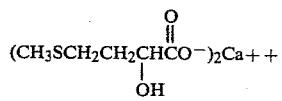

(hereinafter referred to as the product calcium salt) can be prepared by contacting α-hydroxy-γ-methylmercaptobutyric acid (hereinafter referred to as MHBA) in the liquid phase at a temperature of about 25° to 120° C. with solid calcium oxide or calcium hydroxide and mixing the resulting reaction mass at a temperature of about 45° to 130° C. to form the product calcium salt.

Utilization of this novel process offers many advantages over the standard processes for preparing the product calcium salt: it leads to higher yields, reduces waste loads and eliminates the energy-intensive step of evaporation.

DETAILED DESCRIPTION OF THE INVENTION

The MHBA used in the process of this invention and methods for preparing it are known in the art. A preferred process for preparing MHBA is taught in U.S. Pat. No. 3,773,927, the disclosure of which is hereby incorporated by reference. This patent teaches the hydrolysis of α-hydroxy-γ-methylmercaptobutylronitrile with hydrochloric acid to yield an aqueous slurry of ammonium chloride containing MHBA in the liquid phase. The solution of MHBA prepared according to U.S. Pat. No. 3,773,927, after concentration and filtration, can be used in the process of this invention. Preferably, the solid free solution will contain about 75 to 92% MHBA by weight and about 3 to 20% water, and, more preferably, about 85 to 90% MHBA by weight and 6% to 12% water. It will be appreciated that the MHBA used in this invention may be prepared by other known methods as well.

A minimum of one equivalent of calcium oxide or hydroxide is used for every one equivalent of MHBA in preparing the product calcium salt. When the MHBA has been prepared as described in U.S. Pat. No. 3,773,927, the MHBA solid free solution will contain ammonium chloride which will also react with the calcium oxide or hydroxide. Thus, an additional equivalent of calcium compound for each equivalent of ammonium chloride should be used. To insure full reaction with the MHBA it is preferred to use a slight excess of the calcium compound. An excess of no greater than about 10% is preferred in order to prevent reduction of product purity.

The MHBA solution is preferably added directly to the dry, solid calcium oxide or hydroxide in a solids-type mixer to produce the product calcium salt. The specific conditions employed determine whether this product must be subjected to a separate drying step before it is suitable for commercial use.

When the MHBA is added directly to the calcium oxide or hydroxide, the resulting reaction mass can become very viscous and difficult to mix. It has been found that this problem can be avoided by mixing the calcium oxide or hydroxide with a heel of the dry product calcium salt prior to the addition of the MHBA. In this preferred modification of the process, the reaction mass is a free-flowing powder throughout the reaction cycle, and mixing is relatively easy.

The quantity of heel (product calcium salt) added to the calcium oxide or hydroxide can constitute up to about 80% by weight of the entire reaction mass (the reaction mass constituting calcium oxide or hydroxide, MHBA and the heel of product). Preferably, the quantity of heel will constitute about 20 to 40% by weight of the entire reaction mass.

In a continuous modification of the claimed process, a portion of the calcium salt produced is recycled to a twin rotor mixer or similar piece of apparatus. The calcium oxide or hydroxide is added to the agitated product calcium salt as it moves through the system. After sufficient mixing has taken place, the MHBA is added and the reaction occurs as the reaction mass continues through the system. Exiting product is dried if necessary and a portion is recycled to the start of the system as described above. The amount of heel recycled in this continuous process can vary from about 10% to 80% of the product produced, preferably about 25 to 50%.

In a batch operation, the MHBA is preferably added to a heel containing calcium oxide or hydroxide over a period of about 0.3 to 4 hours, more preferably about 0.5 to 2 hours. After MHBA addition is complete, the reaction mass is mixed for an additional 0.3 to 2 hours to insure completion of the reaction. In a continuous operation, the time elapsing between MHBA addition and the exiting of the product calcium salt, the residence time, is about 0.3 to 2 hours, preferably about 0.5 to 1 hour.

The MHBA solution is maintained at a temperature of about 25° to 120° C. and preferably at a temperature of about 50° to 100° C. during the addition cycle. The resulting reaction mass is maintained at a temperature of about 45° to 130° C., preferably about 80° to 120° C., by external heating or cooling as necessary.

Water is evolved from the reaction mass, the rate of evolution depending on the temperature at which the reaction is performed. The process can be operated at temperatures and residence times such that the product calcium salt exiting the reactor does not require additional drying. Product calcium salt containing no more than about 2% by weight water is suitable for commercial use and for recycling as described above.

This invention is further illustrated but not limited by the following examples. Unless specified to the contrary, all parts are by weight and all temperatures are in degrees centigrade.

EXAMPLE 1

A batch reaction was performed in a laboratory scale double arm, sigma blade mixer. The mixing chamber was open to the atmosphere, and dust and vapors were removed through a scrubbing system.

A powdered mixture consisting of 456 parts of a wetcake of the calcium salt of α-hydroxy-γ-methylmercaptobutyric acid (12.3% water) and 126 parts calcium hydroxide was added to the mixing chamber. Mixing was commenced and the chamber was heated with low pressure steam to 85°–90° C. From an addition funnel, 522 parts MHBA solution (91% MHBA, 7% $H_2O$, 2% $NH_4Cl$) at 90°–100° C. were added, dropwise, over 40 minutes. The heel of Hydan ® wetcake comprised 41% by weight of the total reaction mass. The equivalent ratio of the calcium hydroxide to the equivalents of MHBA plus ammonium chloride was 1.01:1.

When the MHBA addition was complete, the reaction mass was mixed for 20 minutes at 85° to 90°. This additional mixing served to partially dry the reaction mass.

The resulting mixture, containing 6.1% $H_2O$ by weight, was dried in a vacuum oven at 60°. Analysis showed the dry powder to consist of:
96.0% product calcium salt
3.3% chloride salt
0.5% $H_2O$
<0.2% $Ca(OH)_2$ The product is suitable for commercial use.

The reaction described in Example 1 may, of course, be modified in a number of ways.

EXAMPLE 2

A batch reaction is performed in a laboratory scale double arm, sigma blade mixer. The mixing chamber is open to the atmosphere, dust and vapors being removed through a scrubbing system. This example differs from Example 1 in that dry calcium salt of MHBA is used as a heel, calcium oxide is used instead of the hydroxide, and the mixture is dried while mixing.

A heel of 342 parts dry product is charged to the mixing chamber. To this, 97 parts of calcium oxide is added. Mixing is commenced and the chamber is heated with low pressure steam. From an addition funnel, 522 parts of MHBA solution (89% MHBA equivalent, 2% $NH_4Cl$) at 95° C. is added dropwise over 20 minutes.

The heel of Hydan ® comprises 35% of the total reaction mass. The equivalent ratio of the calcium hydroxide to the MHBA equivalents and ammonium chloride is 1.05:1.0.

After the MHBA addition is complete, the reaction mass is mixed for 60 minutes at 85°–90° C. The total mixing time is 1.2 hour.

The dry product is suitable for commercial use. Its composition is about:
~95% product calcium salt
~3% chloride salt
~1.0% $Ca(OH)_2$
~0.5% $H_2O$

EXAMPLE 3

A continuous reaction may be performed in a twin rotor mixer as described below:

Calcium hydroxide is added at a rate of 113 parts/hr. to a heel of product recycle. The throughput of the product recycle is 200 parts/hr. To this well-agitated mixture, a solution of MHBA (89% MHBA, 2% $NH_4Cl$, 9% $H_2O$) is added at a rate of 460 parts/hr. The ratio of equivalents of calcium hydroxide to total equivalents of MHBA plus $NH_4Cl$ is 1.05:1. The recycled product comprises 25% by weight of the reaction mass.

The average residence time in the mixer is about 30 minutes. The mixing chamber is heated to maintain the reaction mass at 85° to 90°. The reaction mass leaves the mixer as a wet powder and is continuously dried. A portion, 200 parts/hr., is recycled back to the mixer.

The dried mixture is suitable for commercial use and consists of:
~95% product calcium salt
~3% chloride salt
~1% $Ca(OH)_2$
~0.5% $H_2O$

What is claimed is:

1. A process for preparing the calcium salt of α-hydroxy-γ-methylmercaptobutyric acid (MHBA) which comprises forming a reaction mass by contacting an aqueous solution of MHBA in the liquid phase at a temperature of about 25° to 120° C. with solid calcium oxide or calcium hydroxide, mixing the resulting reaction mass at a temperature of about 45° to 130° C., and recovering therefrom the product calcium salt of MHBA.

2. The process of claim 1 wherein the solution of MHBA in the liquid phase and the calcium oxide or calcium hydroxide are contacted in the presence of a heel of the product calcium salt of MHBA, the amount of heel comprising up to about 80% by weight of the total reaction mixture of MHBA solution, calcium oxide or hydroxide and heel of product calcium salt.

3. The process of claim 2 wherein the heel comprises between about 20 to 40% by weight of the total reaction mass.

4. The process of claim 2 or 3 wherein
   (a) the heel of product calcium salt of MHBA is combined with the calcium oxide or calcium hydroxide, and
   (b) the MHBA is contacted with the mixture prepared in (a).

5. The process of claim 1 wherein the equivalence ratio of calcium oxide or calcium hydroxide to MHBA is at least 1:1.

6. The process of claim 1 wherein the temperature of the solution of MHBA is about 50° to 100° C.

7. The process of claim 1 wherein the reaction mass is mixed at a temperature of about 80° to 120° C.

8. A process for preparing the calcium salt of MHBA which comprises:
   (a) contacting solid calcium oxide or calcium hydroxide with a heel of the product calcium salt of MHBA;
   (b) forming a reaction mass by contacting the mixture prepared in step (a) with a solution of MHBA in the liquid phase at a temperature of about 25° to 120° C.;

(c) mixing the resulting reaction mass at a temperature of about 45° to 130° C.;

(d) recovering therefrom the product calcium salt of MHBA; and (e) recycling a portion of said salt for use in step (a).

9. The process of claim 8 wherein the heel of product calcium salt of MHBA comprises up to about 80% by weight of the total reaction mixture of MHBA solution, calcium oxide or hydroxide and heel of product calcium salt.

10. The process of claim 9 wherein the heel of product calcium salt comprises between about 20 to 40% by weight of the total reaction mixture.

11. The process of claim 8 wherein the equivalence ratio of calcium oxide or calcium hydroxide to MHBA is at least 1:1.

12. The process of claim 8 wherein the mixture prepared in step (a) is contacted with a solution of MHBA in the liquid phase at a temperature of about 50° to 100° C.

13. The process of claim 12 wherein the reaction mass is mixed at a temperature of about 80° to 120° C.

14. A process for preparing the calcium salt of MHBA which comprises:

(a) contacting solid calcium oxide or calcium hydroxide with a heel of the product calcium salt of MHBA, said heel comprising between about 20 to 40% by weight of the total reaction mass of step (b);

(b) forming a reaction mass by adding a solution of MHBA in the liquid phase at a temperature of about 50° to 100° C. to the mixture prepared in step (a), the equivalence ratio of calcium oxide or calcium hydroxide to MHBA in the reaction mass being at least 1:1;

(c) mixing the resulting reaction mass at a temperature of about 80° to 120° C.;

(d) recovering therefrom the product calcium salt of MHBA; and (e) recycling a portion of said salt for use in step (a).

* * * * *